(12) United States Patent
Fukuda et al.

(10) Patent No.: US 8,841,612 B2
(45) Date of Patent: Sep. 23, 2014

(54) CHARGED PARTICLE BEAM MICROSCOPE

(75) Inventors: Muneyuki Fukuda, Kokubunji (JP);
 Naomasa Suzuki, Hitachinaka (JP);
 Tomoyasu Shojo, Saitama (JP);
 Noritsugu Takahashi, Kokubunji (JP);
 Hiroshi Suzuki, Koganei (JP); Hiroshi Makino, Chino (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/812,899

(22) PCT Filed: Aug. 8, 2011

(86) PCT No.: PCT/JP2011/068091
 § 371 (c)(1),
 (2), (4) Date: Jan. 29, 2013

(87) PCT Pub. No.: WO2012/039206
 PCT Pub. Date: Mar. 29, 2012

(65) Prior Publication Data
 US 2013/0126733 A1 May 23, 2013

(30) Foreign Application Priority Data
 Sep. 25, 2010 (JP) .................................. 2010-214595

(51) Int. Cl.
| | |
|---|---|
| *G01N 23/00* | (2006.01) |
| *H01J 23/00* | (2006.01) |
| *H01J 37/26* | (2006.01) |
| *H01J 37/22* | (2006.01) |
| *H01J 37/28* | (2006.01) |
| *G01K 7/00* | (2006.01) |
| *G01N 23/22* | (2006.01) |

(52) U.S. Cl.
 CPC ............... *H01J 37/263* (2013.01); *G01N 23/22* (2013.01); *H01J 37/222* (2013.01); *H01J 37/28* (2013.01)
 USPC .......................................................... 250/306

(58) Field of Classification Search
 USPC .......................................................... 250/306
 See application file for complete search history.

(56) References Cited

U.S. PATENT DOCUMENTS

| | | | |
|---|---|---|---|
| 5,160,884 | A | 11/1992 | Todokoro et al. |
| 5,466,940 | A | 11/1995 | Litman et al. |
| (Continued) | | | |

FOREIGN PATENT DOCUMENTS

| | | | |
|---|---|---|---|
| JP | 3-229179 A | 10/1991 | |
| JP | 6-96711 A | 4/1994 | |
| (Continued) | | | |

OTHER PUBLICATIONS

International Search Report with English translation dated Aug. 30, 2011 (four (4) pages).

*Primary Examiner* — Nicole Ippolito
*Assistant Examiner* — Sean Luck
(74) *Attorney, Agent, or Firm* — Crowell & Moring LLP

(57) ABSTRACT

This charged particle beam microscope is characterized by being provided with selection means (153, 155) for a measurement processing method for detected particles (118) and by this means selecting a different measurement processing method for a scanning region with a large number of secondary electrons (115) emitted from a sample (114) and for a region with a small number of secondary electrons. Thus, in sample scanning using a charged particle beam microscope, an image in which the contrast of bottom holes and channel bottoms with few emitted secondary electrons is emphasized and images that emphasize shadow contrast can be acquired in a short period of time.

5 Claims, 8 Drawing Sheets

(56) References Cited

U.S. PATENT DOCUMENTS

| | | | |
|---|---|---|---|
| 6,051,834 A * | 4/2000 | Kakibayashi et al. | 250/311 |
| 6,501,077 B1 | 12/2002 | Sawahata et al. | |
| 2003/0111602 A1* | 6/2003 | Sato et al. | 250/310 |
| 2006/0065844 A1 | 3/2006 | Zelakiewicz et al. | |
| 2006/0151700 A1 | 7/2006 | Honda et al. | |
| 2006/0186351 A1 | 8/2006 | Nishiyama et al. | |
| 2007/0181807 A1* | 8/2007 | Fukuda et al. | 250/310 |
| 2008/0099673 A1 | 5/2008 | Fukuda et al. | |
| 2009/0008550 A1* | 1/2009 | Nakano et al. | 250/310 |
| 2009/0266985 A1 | 10/2009 | Nakahira et al. | |
| 2010/0084568 A1* | 4/2010 | Lagarec et al. | 250/397 |
| 2011/0303843 A1* | 12/2011 | Omori et al. | 250/307 |
| 2012/0004879 A1* | 1/2012 | Fukuda et al. | 702/83 |
| 2013/0015351 A1* | 1/2013 | Kooijman et al. | 250/307 |
| 2013/0129200 A1* | 5/2013 | Yamada et al. | 382/159 |

FOREIGN PATENT DOCUMENTS

| | | |
|---|---|---|
| JP | 8-273569 A | 10/1996 |
| JP | 2001-148230 A | 5/2001 |
| JP | 2006-105977 A | 4/2006 |
| JP | 2006-196281 A | 7/2006 |
| JP | 2006-228999 A | 8/2006 |
| JP | 2008-108592 A | 5/2008 |
| JP | 2009-245674 A | 10/2009 |
| JP | 2010-182549 A | 8/2010 |
| WO | WO 00/19482 A | 4/2000 |

* cited by examiner

FIG. 1
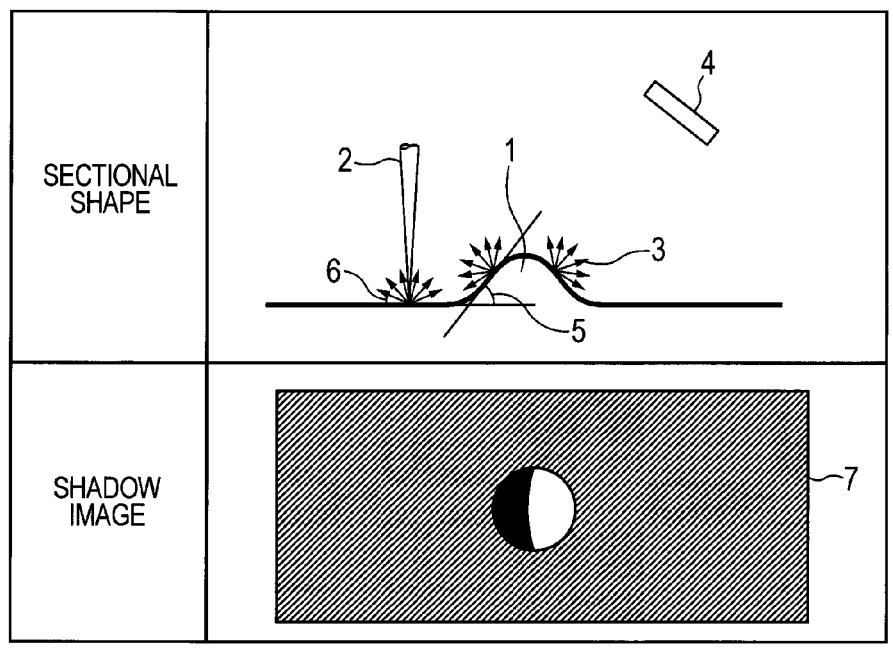
FIG. 2A
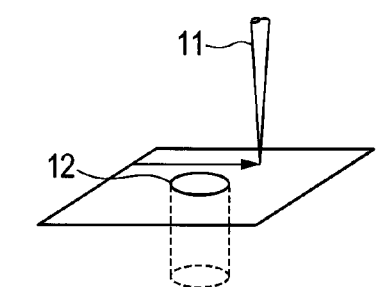
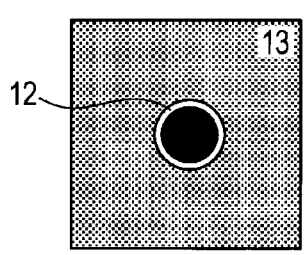
FIG. 2B
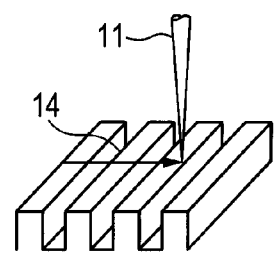
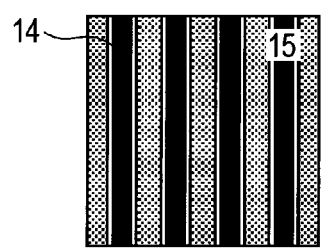

CHARGED PARTICLE BEAM MICROSCOPE

TECHNICAL FIELD

The present invention relates to a charged particle beam microscope of observing and inspecting a fine circuit pattern of a semiconductor device, a liquid crystal or the like by a charged particle beam.

BACKGROUND ART

First, in accordance with finely structural and integrated forming of a semiconductor device, management of lithography steps has been more and more increased a request for measuring a fine pattern of a size of several tens nm formed on a wafer with high accuracy and at high speed, and a Critical Dimension Scanning electron Microscope (hereinafter, CD-SEM) is a measurement device which is indispensable for an accuracy of a semiconductor. In recent years, a need for measuring a two-dimensional pattern has also been increased in addition to a need for measuring a line width of a standard line and space (L&S) pattern. The measurement of the two-dimensional pattern is realized by comparing an SEM image with LSI layout data of a format of GDSII or the like which is a de facto standard for describing a mask pattern of a semi-conductor. In the management of lithography steps, enormous LSI layout data, observation points which are necessary for measuring a two-dimensional pattern may also be as many as several tens thousands points/chip, and there are also high needs for shortening time periods of move/image acquire/measure: Move Acquire Measure (hereinafter, MAM). Design For Manufacturing Scanning electron Microscope (hereinafter, DFM-SEM) which can meet the needs described above is needed.

Japanese Unexamined Patent Application Publication No. 2006-196281 (Patent Literature 1) discloses a method of holding an adjusted value of a gain of a detector or a detection algorithm by setting plural beam currents and switching the beam currents at high speed in order to make S/N and shortening of an image taking time period compatible with each other by switching the beam currents at a scanning electron microscope.

Japanese Unexamined Patent Application Publication No. Hei3-229179 (Patent Literature 2) discloses a method of improving S/N of a signal by calculating a sum of sampling values at plural points of pulses of secondary electron signals.

Japanese Unexamined Patent Application Publication No. 2006-105977 (Patent Literature 3) discloses an imaging system including a detector adjusting circuit which determines an operation parameter of a detector on which a radiation is incident from a radiation source based on the incident radiation.

Second, a semiconductor device is fabricated by repeating steps of transcribing a pattern formed on a wafer by a photomask by a lithography processing and an etching processing. In such a fabrication process, it is indispensable to swiftly analyze a defect discovered by an in-line wafer inspection and utilize the analysis for the countermeasure in order to realize an increase in a yield at an early stage and stable operation of a fabrication process. A technology of reviewing a large number of detection defects and classifying the detection defects according to causes of defect occurrence is needed to link an inspection result swiftly to a countermeasure against a failure.

However, a defect size which effects an influence on a fabrication yield of a semiconductor is made to be fine in accordance with fine structure formation of a fabrication process. According to an optical reviewing device of a background art, it is difficult to review and classify a small defect owing to a deficiency in a resolution. A review device of an SEM (Scanning Electron Microscope) type capable of reviewing a small defect with high resolution is therefore used. According to the device, it is important to acquire a shadow image by an SEM image that is equivalent with a shadow image produced when a light beam is cast sideways in order to detect recesses and protrusions of a small foreign matter, a scratch or the like.

An explanation will be given of a general principle for acquiring such a shadow image in reference to FIG. 1. For example, when a recessed and protruded portion 1 at a sample surface that is caused by, for example, a foreign matter in a film is scanned by an electron beam 2, secondary particles (secondary electrons) 3 are emitted at respective irradiation points on the sample. Here, an energy of the secondary electron 3 emitted has a distribution, a component having a comparatively low energy (low speed component) is referred to as a secondary electron (SE), and a component having a comparatively high energy (high speed component) is referred to as a back scattering electron (BSE). Secondary particles at a generated portion have elevation angle components in various directions as indicated by numeral 6 of FIG. 1 by an arrow mark. Here, the elevation angle of the secondary particle at the generated portion signifies an angle which is made by each elevation angle component of the secondary particle relative to a plane at which an optical axis of the irradiated primary beam becomes a normal line. When attention is paid to a certain one of the elevation angle component 6 of the secondary particle at the generated portion, although the second particle which is emitted to the right side reaches a detector 4, the secondary particle which is emitted to the left side does not reach the detector. An amount of detecting a secondary electron at the detector 4 therefore differs by an inclination angle 5 of the recessed and protruded portion of the sample surface at the generated portion of the secondary particle. As the result, a shadow contrast in accordance with the recesses and protrusions of the sample surface appears at a shadow image 7 that is acquired by the detector.

Japanese Unexamined Patent Application Publication No. Hei8-273569 (Patent Literature 4) discloses a technology with regard to a charged particle beam column which improves a measurement accuracy of a sample by separating to detect a low speed component (SE) and a high speed component (BSE) of a secondary particle in an optical system of detecting a secondary charged particle using an electromagnetic superposing type objective lens. According to the technology disclosed in the publication, the low speed component and the high speed component are separated to detect by detecting BSE at an inner side ring-like band and SE at an outer side ring-like band by a ring-like detector provided between an electron source and an objective lens by utilizing the fact that trajectories of the low speed component and the high speed component of the secondary particle differ from each other. Since the outer side ring-like band is divided into four in a fan shape and an azimuthal angle of a secondary electron can be selected at an emitting position, a shadow image can be acquired.

On the other hand, International Publication No. WO00/19482 pamphlet (Patent Literature 5) discloses a configuration for separating to detect a low angle component and a high angle component of a secondary particle. According to the configuration disclosed in the publication, a secondary particle detector for detecting a low angle component on an upper side of an objective lens is provided, a reflecting plate for impinging the low angle component of the generated secondary particle between the detector for detecting the low angle component and the objective lens is arranged, a subsidiary particle generated by impinging the low angle component particle is guided to a secondary particle detector for detecting the low angle component by an E×B deflector, and accordingly, the low angle component of a reflected electron and a secondary electron are detected. With regard to a high angle component of the reflected electron, a separate secondary particle detector detecting the high angle component and a second E×B deflector are provided on an upper stage (electron source side) of the E×B deflector to detect only the high angle component by the detector for the high angle component.

Japanese Unexamined Patent Application Publication No. 2006-228999 (Patent Literature 6) discloses an electron microscope which is provided with a ring-like detector between an electron source and an objective lens for selecting to detect a low angle component and a high angle component of an elevation angle, and an azimuthal angle component of a secondary electron generated.

CITATION LIST

Patent Literature

Patent Literature 1: Japanese Unexamined Patent Application Publication No. 2006-196281
Patent Literature 2: Japanese Unexamined Patent Application Publication No. Hei3-229179
Patent Literature 3: Japanese Unexamined Patent Application Publication No. 2006-105977
Patent Literature 4: Japanese Unexamined Patent Application Publication No. Hei8-273569
Patent Literature 5: International Publication No. WO00/19482 pamphlet
Patent Literature 6: Japanese Unexamined Patent Application Publication No. 2006-228999

SUMMARY OF INVENTION

Technical Problem

FIG. 2A and FIG. 2B show an example of a method of observing a hole or a groove that is frequently formed on an Si wafer by a Scanning Electron Microscopy (hereinafter, SEM) when a circuit pattern of a semiconductor device is formed, FIG. 2A shows a case of a hole and FIG. 2B shows a case of a groove. In recent years, fine structure formation of a circuit pattern is progressed such that a size of a hole or a groove may also become about 10 nm when the size is small. A probe diameter of an electron beam for a simple and convenient observation of a sample surface has therefore been contracted year by year to reach about 1 nm (about 1/10 of pattern size), which configures apparatus or ways of acquiring an observed image with high resolution successive to a resolution of a Scanning Probe Microscopy (hereinafter, SPM) having an atom resolution. An observed circuit pattern is configured by a hole or a groove that is formed at an insulating film, a semiconductor, or a conductor film. When an aspect of a processed shape is a high, the number of secondary electrons emitted from a hole bottom or a groove bottom becomes remarkably smaller than that of other scanning region. A hole bottom observation image 13 which is obtained by scanning an electron beam 11 is configured by a white band of a contour line 12 of the hole and a dark circular region of the hole bottom. On the other hand, a groove bottom observation image 15 is configured by a white band at a contour line 14 of the groove and a dark band-like region at the groove bottom.

All of the background arts described in Patent Literatures 1 through 3 cannot avoid a problem that when the number of the second electrons emitted from the hole bottom or the groove bottom becomes remarkably smaller than that of the other scanning region, an image taking time period is remarkably prolonged, and a contrast of the observed image is reduced.

It is a first object of the present invention to provide a charged particle beam microscope which can acquire an image emphasizing a contrast of a hole bottom or a groove bottom in inspecting various samples of a semiconductor device, a magnetic disk and the like in a short period of time.

A secondary particle generated by irradiating an electron beam can grossly be classified into 4 ways (low angle component and low speed component, low angle component and high speed component, high angle component and low speed component, high angle component and high speed component) by an elevation angle (low angle component and high angle component) and an energy (low speed component and high speed component) at a generated portion. In the secondary particle, the high speed component includes a large number of pieces of information with regard to a shape of a generated portion of the secondary particle. On the other hand, the low speed component includes a large number of pieces of information of an inner portion of a sample in a range in correspondence with an invasion depth of the primary beam (for example, material, composition or the like of sample). When an image can be formed by discriminating to detect a secondary particle that is generated by irradiating a primary beam into a low speed component and a high speed component, the image is advantageous for observing the sample. The image formed by the high speed component may be referred to as a shadow image.

However, a detecting signal of a secondary particle is attenuated and a contrast of an observed image is reduced by discriminating the signal. All of the background arts described in Patent Literatures 4 through 6, have a configuration which can separate to detect the secondary particle by dividing the secondary particle into the low angle component and the high angle component; however, the high angle component of the elevation angle at the generated portion of the high speed component included in the secondary particle cannot adequately be separated from the low speed component. As the result, the high elevation angle component of the high speed component is deleted from the shallow image, an intensity of a contrast of the shadow image is weaker than a value inherently to be acquired, and a shape having a small (shallow) degree of recesses and protrusions does not appear in the shallow image.

Since only a shallow image having a weak contrast can be acquired, an image data is obliged to be integrated at the number of times in order to gain an S/N ratio of the image, and an image of a quality necessary for inspecting or measuring a sample cannot be acquired in a short period of time. Although when a current value of a primary beam is increased, an image signal having a large S/N can be acquired, when the current value is increased, a beam diameter is increased and a resolution of an acquired image is deteriorated.

Hence, it is a second object of the present invention to provide a charged particle beam microscope which can acquire an image emphasizing a shadow contrast in a short period of time in inspecting various samples of a semiconductor device, a magnetic disk and the like.

Solution to Problem a charged particle beam microscope includes a charged particle source, a stage of mounting a sample, a charged particle optical system of irradiating the sample on the stage with a beam of a charged particle generated by the charged particle source, a detector of detecting a detected particle from the sample caused by the beam, and controlling means for controlling these, further including a beam dwell integration selector of determining a beam dwell integration method of detecting the detected particle caused by the beam, a beam dwell integrator of carrying out an integration in accordance with a determination of the beam dwell integration selector, a selector of a frame integration of determining the frame integration method, and a frame integrator of carrying out an integration in accordance with a determination of the selector of the frame integration as one embodiment for achieving the above-described objects.

Advantageous Effects of Invention

A charged particle beam microscope can acquire an image of emphasizing contrasts of a hole bottom and a groove bottom in a short period of time, or a charge particle beam microscope can acquire an image of emphasizing a shadow contrast in a short period of time in inspecting various samples such as a semiconductor device and a magnetic disk when the beam dwell integration selector of determining the beam dwell integration method and the selector of the frame integration of determining the frame integration method are included in the microscope.

BRIEF DESCRIPTION OF DRAWINGS

FIG. 1 is an outline view for explaining a general principle for acquiring a shadow image of a surface of an observed sample by using an electron beam, the upper stage shows a sectional shape of a sample, and the lower stage shows a shadow image.

FIG. 2A is an outline view for explaining a method of observing a hole pattern by using a scanning microscope, the upper stage shows a perspective view of a surface of a sample, and the lower stage shows a schematic view of an SEM image.

FIG. 2B is an outline view for explaining a method of observing a groove pattern by using a scanning electron microscope, the upper stage shows a perspective view of a surface of a sample, and the lower stage shows an SEM image.

DESCRIPTION OF EMBODIMENTS

Figure 3:
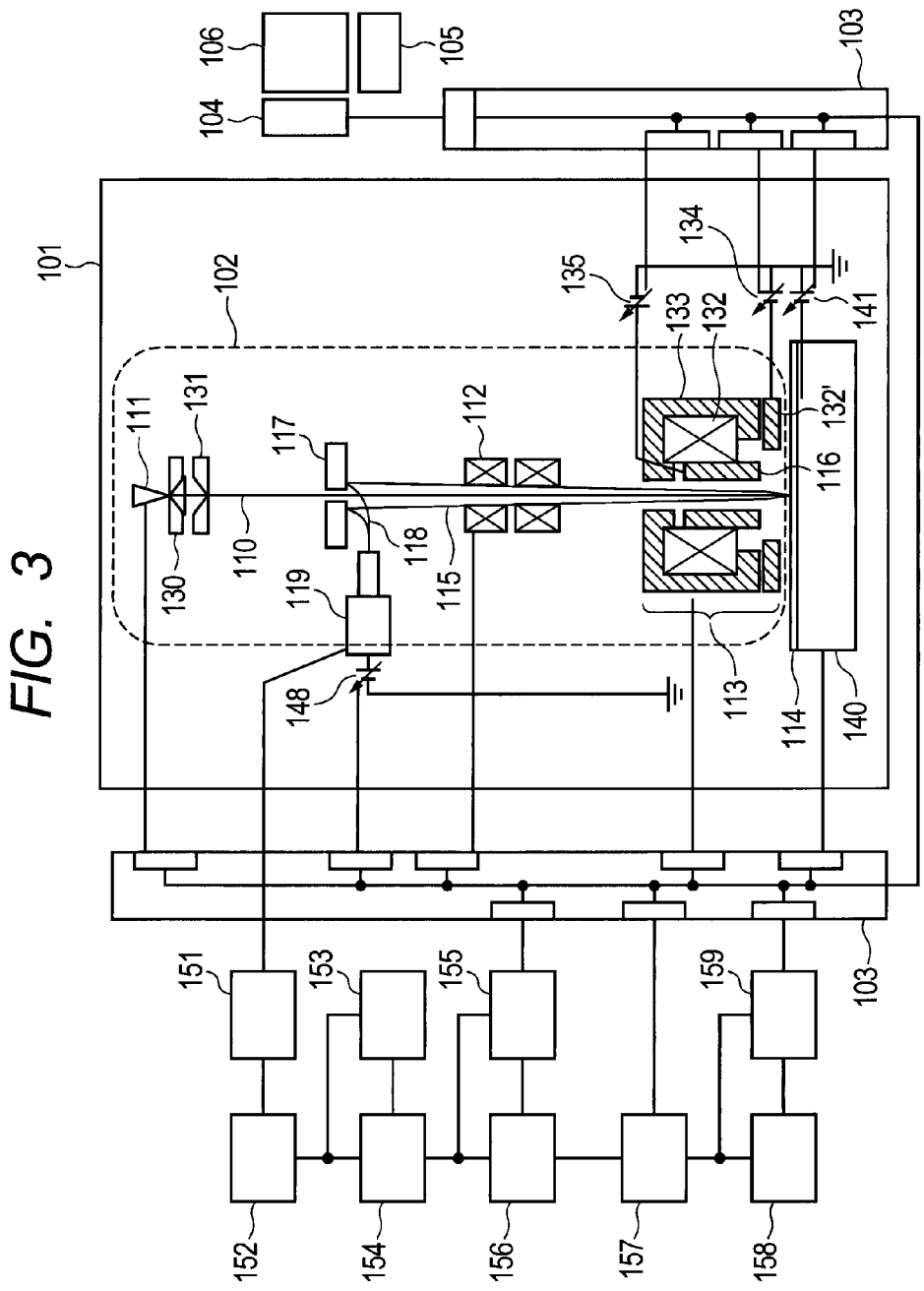
FIG. 3 is a schematic view showing a total configuration of a charged particle beam microscope (scanning electron microscope) according to a first embodiment.

In a scanning region in which the number of secondary electrons (number of secondary particles) is small, a detecting signal is configured by a pulse-like waveform in which pulses are discrete from each other. The small number of secondary electrons produces a state in which two or more electrons are hardly present in a time resolution (pulse width) of a detector. The region is referred to as a single secondary electron region, and it is known that an electron counting method is effective in the region. A quantum efficiency which becomes important in the electron counting method is a probability of generating an electron when one piece of electron is incident on a detector. In the single secondary electron region, since the number of emitted electrons per one electron is only 1 or 0, the number of emitted electrons per unit time can be counted. The region is referred to electron counting region, and the signal detecting method is referred to as an electron counting system in contrast to an analog system which measures the number of electrons by signal intensity.

That is, since in a secondary electron generating procedure at a sample and a signal amplifying procedure at a detector, a signal is generated by a statistic probability that is represented by a Poisson distribution, a noise of an AC component superposed is brought about on the signal. In the electron counting method, S/N is improved by an amount of a noise factor of the detector in comparison with the analog method. In the electron counting method, S/N of the observed image is improved by detecting a signal by the electron counting method in a scanning region in which the number of secondary electrons is small.

On the other hand, a method of prolonging image taking time other than detecting a signal by an electron counting method is used as apparatus or means effective for improving S/N of the observed image when the number of secondary electrons is small. The image taking time can be shortened by reducing the number of pixels of a taken image or increasing a beam current. However, an accuracy of measuring a two-dimensional pattern can be improved by carrying out a highly fine observation by increasing the number of pixels of the taken image. It is known for shortening MAM that not a reduction in the pixel number but an increase in the beam current is effective. At this occasion, a contour line of a two-dimensional pattern sometimes cannot be detected by electrifying a sample by irradiating a beam. This finds that it is effective to reduce a charge injection amount by shortening beam dwell time (hereinafter, Dwell time) per pixel for restraining a sample from being electrified. Since, when the number of charges injected to a sample is reduced by shortening Dwell time, the number of secondary electrons which can be detected is reduced, a contrast of an image is deficient. A contrast of an image is improved by compensating for the number of detected secondary electrons by repeating frame integration at each scanning period (hereinafter, loop time). In a scanning region in which the number of emitted electrons per Dwell time is small in a hole bottom or a groove bottom, the scanning region becomes the single secondary electron region in which the detecting signal is configured by a waveform in a pulse-like shape in which respective pulses are discrete from each other. At this occasion, a signal is detected by an electron counting system of counting the number of electrons detected during Dwell time. On the other hand, in a scanning region which does not become the single secondary electron region, a signal is detected by an analog system. Further, in a case where the number of emitted electrons per total pixel dwell time in which Dwell time is multiplied by frame integration at a hole bottom or a groove bottom, numbers of electrons detected during Dwell time are added to each other by frame integration. On the other hand, in a case where the single the electron region is not configured during total pixel dwell time, frame integration is carried out by an analog system.

In accordance with fine structure formation and integrated formation of a semiconductor device, in view of a request for measuring a fine pattern of several tens nm seize formed on a wafer with high accuracy and at high speed in the management of lithography steps, and in view of a case in which observation points necessary for measuring a two-dimensional pattern in enormous LSI layout data are as many as several tens thousands points/chip in the management of the lithography steps, there can be provided DFM-SEM which can meet needs for shortening MAM and needs for intending to visualize a shape of a bottom of a groove or a hole by carrying out an image processing even when an aspect ratio of a groove or a hole of a circuit pattern is large.

According to the charged particle beam microscope of the present invention, there is also an increased need for measuring a two-dimensional pattern in addition to measurement of a line width of a standard line and space (L&S) pattern. The measurement of the two-dimensional pattern is realized by comparing an LSI layout data of a format of GDSII or the like and an SEM image. The management of the lithography steps can correspond to even a case in which the observation points which needs two-dimensional pattern measurement in an enormous LSI layout data are as many as several tens thousands points/chip. When an aspect of a processed shape is large, the number of secondary electrons emitted from a hole bottom or a groove bottom becomes remarkably smaller than that of the other scanning region. In a scanning region in which the number of secondary electrons is small, the detecting signal is configured by a pulse-like waveform in which pulses are discrete from each other. There can be dealt with even a case of bringing about a state in which two or more electrons are hardly present within a time resolution (pulse width) of the detector when the number of secondary electrons is small.

Although an explanation will mainly be given of an example of applying to a device using a scanning electron microscope in the following embodiments for simplicity, a method of dynamically selecting a system of beam scanning and a signal integration in respective embodiments can be applied to a general charged particle beam device including not only an electron beam device by but an ion beam device. Also, although an explanation will be given of a device in which a sample is configured by a semiconductor wafer in the following embodiments, as a sample used in various kinds of charged particle beam devices, inspection and measurement objects can be configured by various kind of samples such as a semiconductor board, a chipped piece of a wafer formed with a pattern, a chip cut out from a wafer, a hard disk, a liquid crystal panel or the like other than a semiconductor wafer.

First Embodiment

In the first embodiment, an explanation will be given of an example of applying to a scanning electron microscope.

A scanning electron microscope of the present embodiment is configured by an electron optics system formed in a vacuum cabinet, an electron optics system control device arranged at the surrounding, a host computer of supervisingly controlling a total of the apparatus by controlling individual control units included in a control power source, an operation table connected to the control device, displaying means including a monitor for displaying an acquired image and the like. The electron optics system control device is configured by a power source unit for supplying currents and voltages to respective constituent elements of the electron optics system, and signal control lines for transmitting control signals to the respective constituent elements.

FIG. 3 is a schematic diagram showing a total configuration of a scanning electron microscope which is a charged particle beam microscope according to the present embodiment.

The scanning electron microscope according to the present invention is configured by an electron optics system 102 provided at an inner portion of a vacuum cabinet 101, an electron optics system control device 103 arranged at the surrounding, a host computer 104 of supervisingly controlling a total of the apparatus by controlling individual control units included in a control power source, an operation table 105 connected to the control device, displaying means 106 including a monitor of displaying an acquired image. The electron optics system control device is configured by a power source unit for supplying currents and voltages to respective constituent elements of the electron optics system 102, signal control lines for transmitting control signals to the constituent elements and the like.

The electron optics system 102 is configured by an electron source 111 of generating an electron beam (primary charged particle beam 110), a deflector 112 of deflecting the primary electron beam, an electromagnetically superposing type objective lens 113 of converging the electron beam, a booster magnetic path member 116 of converging and dispersing a secondary electron (secondary particle) 115 emitted from a sample 114 held on a stage, a reflecting member 117 for impinging the secondary electron, a central detector 119 of detecting a subsidiary particle (tertiary particle) 118 reemitted by the impingement. The reflecting member 117 is configured by a metal member in a circular disk shape formed with an opening for passing the primary beam, and the bottom face forms a secondary particle reflecting face. Incidentally, notation 135 designates a booster magnetic path power source, and notation 148 designates a central detector power source.

The electron beam 110 emitted from the power source 111 is accelerated by a potential difference formed between a drawing electrode 130 and an accelerating electrode 131, and arrives at the electromagnetically superposing type objective lens 113. The objective lens 113 focuses the incident primary electron beam onto the sample 114 by exciting a magnetic field by a coil 132. A control magnetic path member 132' is supplied with a potential by which a potential relative to a potential of a yoke member 133 becomes negative, and the potential is supplied by a control magnetic path power source 134. A stage 140 is applied with a potential by which a potential difference with the booster magnetic path member 116 becomes negative by a stage power source 141. The electron beam 110 passing through the booster magnetic path member 116 is rapidly decelerated and arrives at a sample surface. Here, a landing energy of the primary beam is determined only by a potential difference between the electron source 111 and the stage 140. When potentials applied to the electron source 111 and the stage 140 are controlled to predetermined values, the landing energy can be controlled to a desired value irrespective of potentials applied to the booster magnetic path member 116 and the acceleration electrode 131. Incidentally, the objective lens 113 may be of any type, for example, a magnetic field lens or an electrostatic lens will do.

The scanning electron microscope is configured by a brightness/contrast control circuit 151 of controlling a brightness and a contrast of a signal waveform detected by the central detector 119, an analog/digital converter 152 of quantizing the signal waveform by time division, a beam dwell integration selector 153 of determining a beam dwell integration method, a beam dwell integrator 154 of integrating a digital signal in accordance with the determination described above, a frame integration selector 155 of determining a frame integrating method, a frame integrator 156 of integrating the digital signal in accordance with the determination described above, an image quality improving processing unit 157 of making an observed image easy to see by a two-dimensional image processing as necessary, a display unit 158 of the observed image, and a preserving unit 159 of the observed image. A signal can be efficiently detected by pertinently switching the signal integrating methods of the beam dwell integrator 154 and the frame integrator 156 in accordance with a signal waveform. However, plural detectors may be provided other than the central detector 119. Particularly, when a high speed component of the secondary electron is detected by separately providing detectors on left and right sides, a shadow can be detected. The secondary electron generated by irradiating the electron beam can grossly be classified by an elevation angle (low angle component and high angle component) and an energy (low speed component and high speed component) at a generated portion to be classified into 4 ways (low angle component and low speed component, low angle component and high speed component, high angle component and low speed component, and high angle component and high speed component). In the secondary electron, the high speed component includes much of information with regard to a shape of a generated portion of a secondary electron, on the other hand, the low speed component includes much of information at an inner portion of a sample in a range corresponding to an invasion depth of the primary beam (for example, material, composition of sample or the like). When an image can be formed by detecting the secondary electron generated by irradiating the primary beam to discriminate to the low speed component and the high speed component, the image is advantageous in observing the sample. The image formed by the high speed component is referred to as a shadow image.

A method of prolonging image taking time other than detecting a signal by an electron counting method is used as effective means for improving S/N of an observed image when the number of secondary electrons is small. The image taking time can be shortened by reducing the number of pixels of the taken image or increasing a beam current. However, not a reduction in the number of pixels but an increase in the beam current is effective for shortening MAM, since an accuracy of measuring a two-dimensional pattern can be improved when the taken image is highly finely observed by increasing the number of pixels. Moreover, it is effective to reduce an electron charge injecting amount by shortening beam dwell time (hereinafter, dwell time) per pixel in order to restrain a sample from being electrified because a contour of a two-dimensional pattern sometimes cannot be detected by electrifying the sample by irradiating the beam. When the number of injecting electric charge is reduced by shortening Dwell time, a contrast of the image becomes deficient since the number of detectable secondary electrons is reduced. The contrast of the image is improved by compensating for the number of detected secondary electrons by repeating frame integration at each scanning period (hereinafter, loop time).

Figure 4:
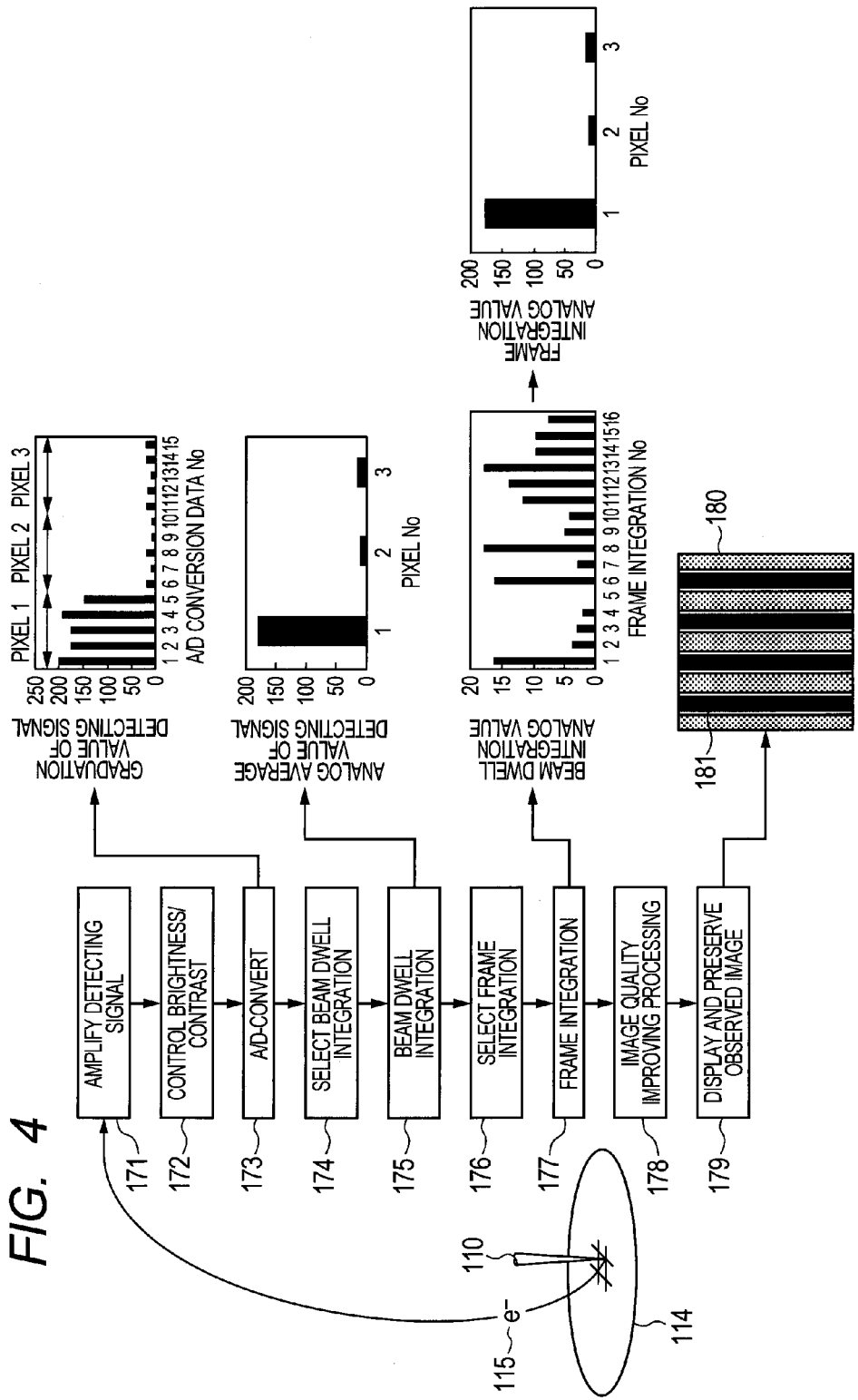
FIG. 4 is a schematic view showing an example of a flowchart when an observed image is acquired by using the scanning electron microscope shown in FIG. 3.

FIG. 4 is a schematic diagram showing a flowchart of acquiring an observed image.

An analog signal is formed at step 171 of amplify detecting signal by collecting the subsidiary particle 118 caused by the secondary particle 115 emitted by irradiating the sample 114 with the electron beam 110 converged by the objective lens by the central detector 119. A signal waveform is put in order by the brightness/contrast control circuit 151 at step 172 of control brightness/contrast. At step 173, the signal waveform is A/D-converted by the A/D converter 152. Incidentally, an example of a data when converted into digital is shown by a bar graph. According to the present embodiment, gradation data of a detecting signal is acquired from A/D-convert 173 of five times per one pixel in correspondence with pixel configuring a taken image. Next, beam dwell integration is selected by the beam dwell integration selector 153 at step 174 in reference to a digital signal waveform and setting of the electron optics system control device 103, and beam dwell integration is carried out by a beam dwell integrator 154 at step 175. Incidentally, an example of data when the beam dwell integration is carried out is shown in a bar graph on the right side. Here, a value of integrating and averaging an analog detecting signal acquired at each pixel is shown with a bar graph. Frame integration is selected at a frame integration selector at step 176, and frame integration is carried out at the frame integrator at step 177. An example of analog data of frame integration is shown by bar graphs on the right side. At a bar graph on the left side, at each pixel No. which allocates a number to a pixel configuring an image, a value of acquiring a beam dwell integration analog value for each frame integration number, and integrating and averaging the beam dwell integration analog value is made to be a frame integration analog value, and the bar graph on the right side shows a relationship between the frame dwell integration analog value and pixel No. After the image quality improving processing unit 157 performs an image improving processing at step 178 as necessary, an observed image is displayed and preserved at the observed image displaying unit and the observed image preserving unit at step 179. When a sample having a deep groove is observed, a groove bottom observing image (schematic view) 180 is configured by a white band at a contour line 181 of the groove and a dark band-like region at the groove bottom.

Figure 5:
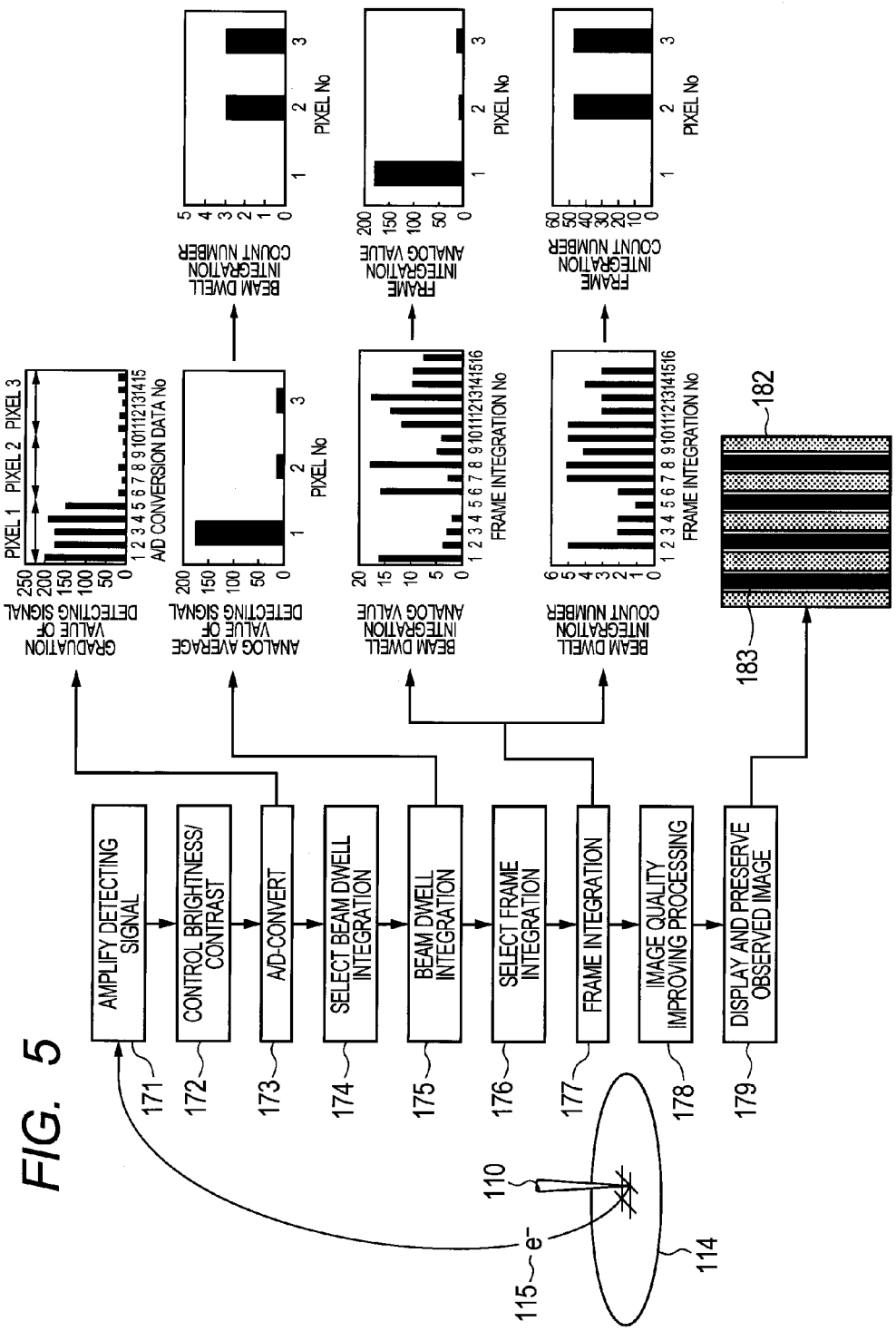
FIG. 5 is a schematic view showing other example of a flowchart when an observed image is acquired by using the scanning electron microscope shown in FIG. 3.

FIG. 5 shows an example of method of easily switching an integration method at each scanning region in a case where plural data is subjected to beam dwell integration to be made to a gradation value of one pixel at step 173 of A/D-convert. As a method of simply and conveniently determining a beam dwell integration method at step 174 of select beam dwell integration, a method of switching an integration method from an analog method to an electron counting means method is effective by providing a threshold for a beam dwell integration value. Data of an analog average value of a detecting signal at pixel No. 1 having a large number of secondary electrons is acquired, and data of a beam dwell integration count number at pixel No. 2 and pixel No. 3 having a small number of secondary electrons at step 175 of beam dwell integration are acquired by carrying out the switching (refer to bar graph on the right side). Thereby, S/N is improved.

Step 176 of select frame integration is carried out at each pixel by being linked with step 174 of select beam dwell integration in addition to the means described above. At step 177, data of a frame integration analog value at pixel 1 having a large number of secondary electrons is acquired, and data of frame integration count number at pixel 2 and pixel 3 having a small number of secondary electrons (refer to a bar graph on the right side) are acquired. Thereby, S/N is improved. As a more highly accurate determining method, there is also a method of determining a single secondary electron region at step 178 of image quality improving processing, switching a beam dwell integration method at an object scanning region, A/D converting at step 173, and reconfiguring an image by recalculating data stored in a memory (preserving unit 159 of observed image) by beam dwell time integration at step 175, frame integration at step 177, and image quality improving processing at step 178. An integration method can effectively be switched at each scanning region by the method described above. S/N of the observed image can be improved by detecting a signal at a scanning region having a small number of secondary electrons by the electron counting method as described above. Also the method of switching to the electron counting method by providing the plural thresholds is also effective. There can also be configured an AC method of emphasizing an AC component of a signal waveform which is intermediate between the analog method and the electron counting method by pertinently setting the threshold (for example, band pass or nonlinear amplification of a detecting signal intensity).

There is also a method of preparing step 171 of amplify detecting signal, step 172 of control brightness/contrast, and step 173 of A/D-convert in parallel for an electron counting method as a method of switching an integration method from an analog method to an electron counting method based on a determination at step 174 of select beam dwell integration. Since a signal waveform can be put in order for the electron counting method, S/N of an observed image can further be improved by detecting a signal at a scanning region having a small number of secondary electrons. When a sample having a deep groove is observed, a groove bottom observing image (schematic view) 182 is configured by a white band at a contour line 183 of the groove and a dark band-like region at the groove bottom at which the signal waveform is put in order by an electron counting method at a scanning region having a small number of secondary electrons.

Figure 6:
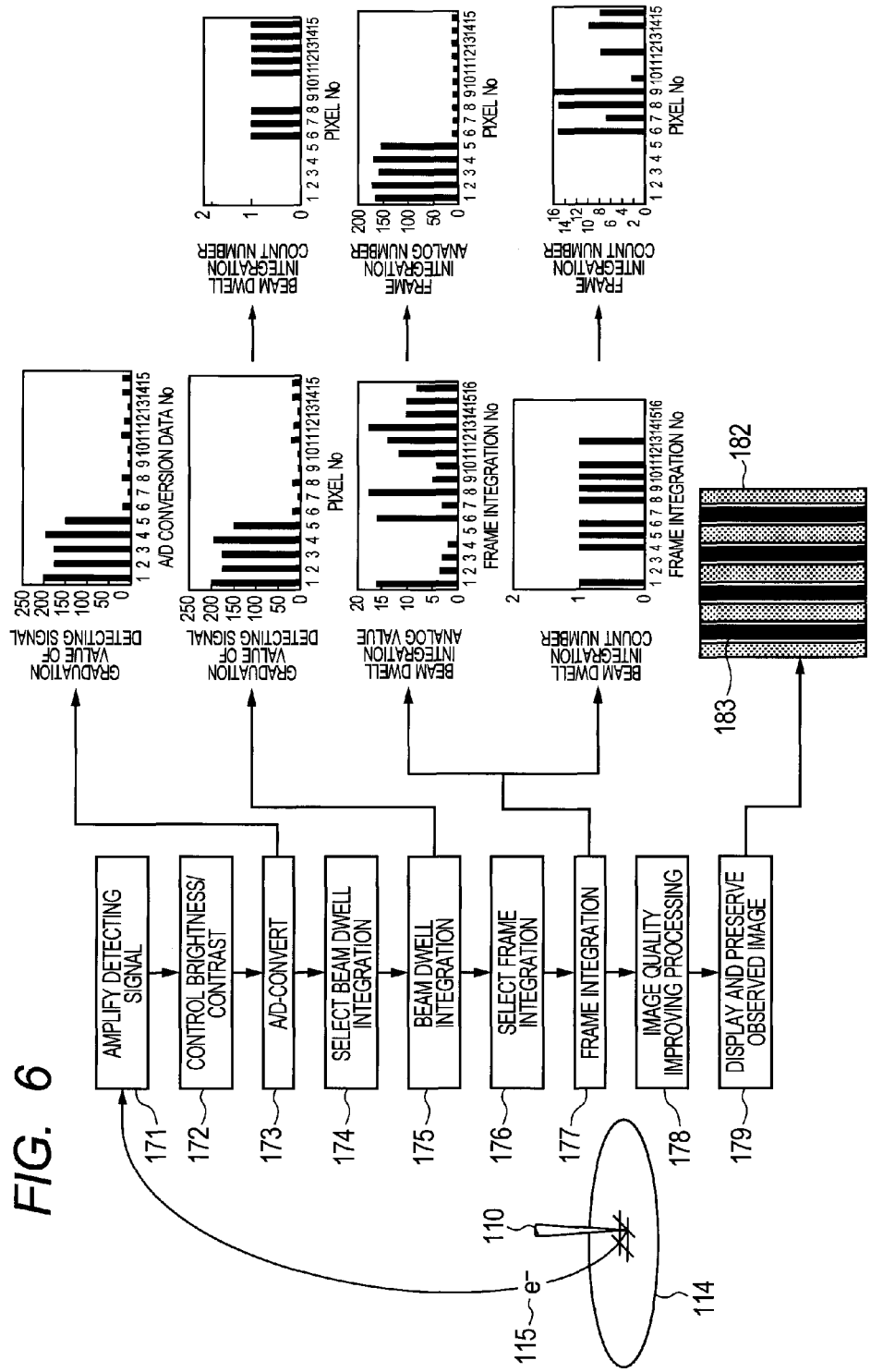
FIG. 6 is a schematic view showing other example of a flowchart when an observed image is acquired by using the scanning electron microscope shown in FIG. 3.

FIG. 6 shows an example of a detecting method in a case of configuring a single secondary electron region at which the number of secondary electrons emitted from a groove bottom or a hole bottom of a sample is small, and only 1 piece of electron can be detected during dwell time. Here, there is used a method of easily switching an integration method at each scanning region in a case where a single data that is A/D-converted at step 173 is made to be a graduation value of 1 pixel by carrying out beam dwell integration. As a method of simply and conveniently determining a beam dwell integration method at step 174 of select beam dwell integration, a method of providing a threshold to a beam dwell integration value outputted when an analog method is used at step 175 of beam dwell integration and switching the integration method from an analog method to an electron counting method is effective. Data of graduation values of detecting signals at pixel No. 1 through pixel No. 5 having a large number of secondary electrons in Pixels configuring an observed image is acquired, and data of beam dwell integration count numbers at pixel No. 6 through pixel No. 15 having a small number of secondary electrons in step 175 of beam dwell integration is acquired by carrying out switching (refer to bar graph on the left side). Thereby, S/N is improved.

It is also effective to select a wave height width of counting at a single secondary electron region in accordance with a noise characteristic of a digital waveform formed at step 171 of amplify detecting signal, step 172 of control contrast/brightness, and step 173 of A/D-convert. Step 176 of select frame integration is carried out at each pixel by being linked with step 174 of select beam dwell integration in addition to the means described above. At step 177, data of frame integration analog values at pixel No. 1 through pixel No. 5 having a large number of secondary electrons are acquired, and data of frame integration count numbers at pixel No. 6 through pixel No. 15 having a small number of secondary electrons (refer to bar graph on right side) are acquired. Thereby, S/N is improved. As a more highly accurate determining method, there is also a method of determining a single secondary electron region at step 178 of image quality improving processing, switching a beam dwell integration method of the object scanning region, A/D-converting at step 173, and reconfiguring an image by recalculating data stored to a memory (preserving unit 159 of observed image) by beam dwell integration at step 175, frame integration at step 177, and image quality improving processing at step 178. An integration method can effectively be switched at each scanning region by the method described above. S/N of an observed image can be improved by detecting a signal at a scanning region having a small number of secondary electrons by the electron counting method described above.

There is also a method of preparing step 171 of amplify detecting signal, step 172 of control brightness/contrast, and step 173 of A/D-convert in parallel for an electron counting method as a method of switching an integration method from an analog method to an electron counting method based on a determination at step 174 of select beam dwell integration. Since a signal waveform can be put in order for an electron counting method, S/N of the observed image can further be improved by detecting a signal in a scanning region having a small number of secondary electrons. When a sample having a deep groove is observed, a groove bottom observation image (schematic view) 182 is configured by a white band at a contour line 183 of a groove and a dark band-like region at a groove bottom.

Figure 7:
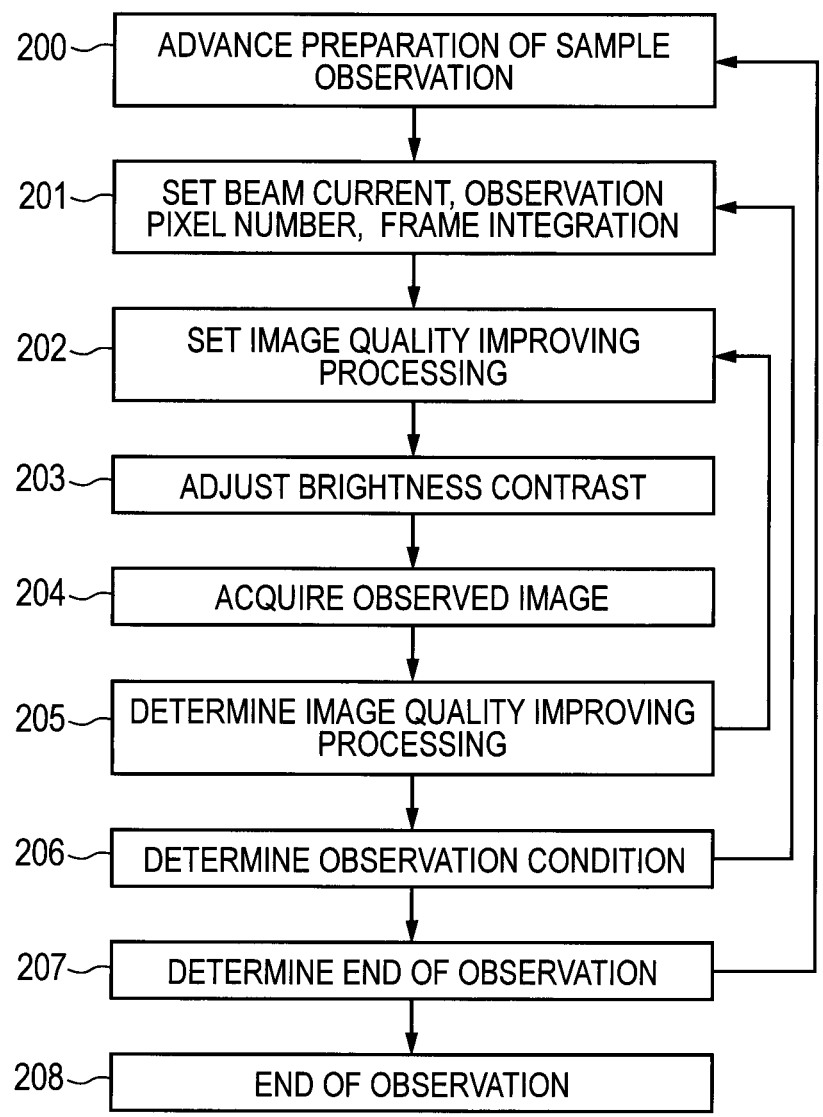
FIG. 7 is a flowchart showing a procedure of setting and executing an observation condition for acquiring an observed image by using the scanning electron microscope shown in FIG. 3.

FIG. 7 shows a setting and executing procedure for acquiring an observed image in accordance with an amount of secondary electrons emitted from a groove bottom or a hole bottom of a sample. A step 200 of advance preparation of sample observation includes that a sample is loaded to a sample chamber, and a state of capable of scanning a beam at a sample observation position is brought about by moving a stage or deflecting a beam. The above-described flow may be proceeded automatically by registering an operation flow or determining an operation content, or may be carried out by a manual. A step 201 of set beam current, observation pixel number, and frame integration includes beam setting of beam acceleration, focal depth or the like and a scanning method of Dwell Time or Loop Time. The above-described flow may be proceeded automatically by registering an operation flow or determining an operation content, or may be carried out by a manual. A step 202 of set image quality improving processing includes an image processing of emphasizing a sharpness or a hole bottom of a groove bottom, or emphasized detection of a hole bottom or a groove bottom by switching detection systems. A step 203 of adjust Brightness Contrast may automatically proceeded to adjust in accordance with the setting 202 of set image quality improving processing or set by a manual. At step 204 of acquire observed image, the observed image in a pertinent state is acquired by carrying out the step 203 of adjust Brightness Contrast under a setting condition of the step 201 of set beam current, observation pixel number, and frame integration. The step 204 of acquire observed image includes step 171 through step 177 of FIG. 4 through FIG. 6. A step 205 of determine image quality improving processing may automatically determined by an effectiveness by an image processing by pertinently emphasizing a contrast of a groove bottom or a hole bottom of a sample in accordance with the step 202 of set image quality improving processing, or may be determined by a manual by viewing an observed image. A step 206 of determined observation condition may determine whether beam setting or scanning method is pertinent, or may automatically be determined by an evaluation value of an image processing of an image S/N or a nonuniformity of an image contrast, or may be determined by a manual by viewing an observed image. A step 207 of determine end of observation may automatically be determined by determining whether a desired observed image can be acquired, and detecting a pattern by comparing an image, or may be determined by a manual by viewing an observed image. A step 208 of end of observation confirms an end of the flow from the step 200 of advance preparation of sample observation until the step 207 of determine end of observation, and proceeds to an external control flow of moving to a next observation point or measurement point, or a manual.

Figure 8:
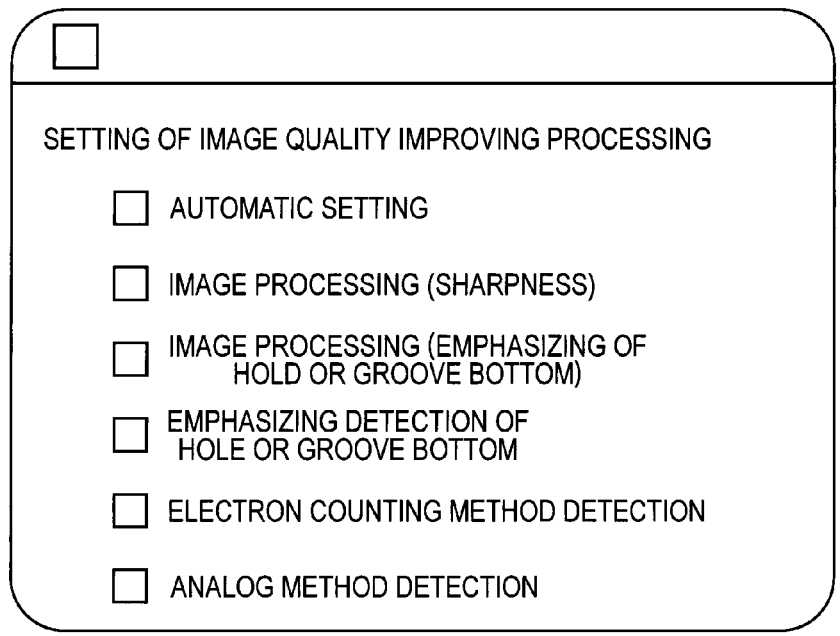
FIG. 8 shows an example of a setting screen in an image quality improving processing when an observed image is acquired by using the scanning electron microscope shown in FIG. 3.

FIG. 8 shows a setting screen displayed on the displaying means 106 at the step 202 of set image quality improving processing of the setting and executing procedure shown in FIG. 7. The setting screen includes items of selecting an image processing of emphasizing a sharpness, a hole bottom and a groove bottom, selecting items with regard to emphasizing detection of the hole bottom and the groove bottom and the signal detecting methods of detection by an electron counting method and detection by an analog method, and a selecting item of automatically setting an image processing and signal detection.

Figure 9:
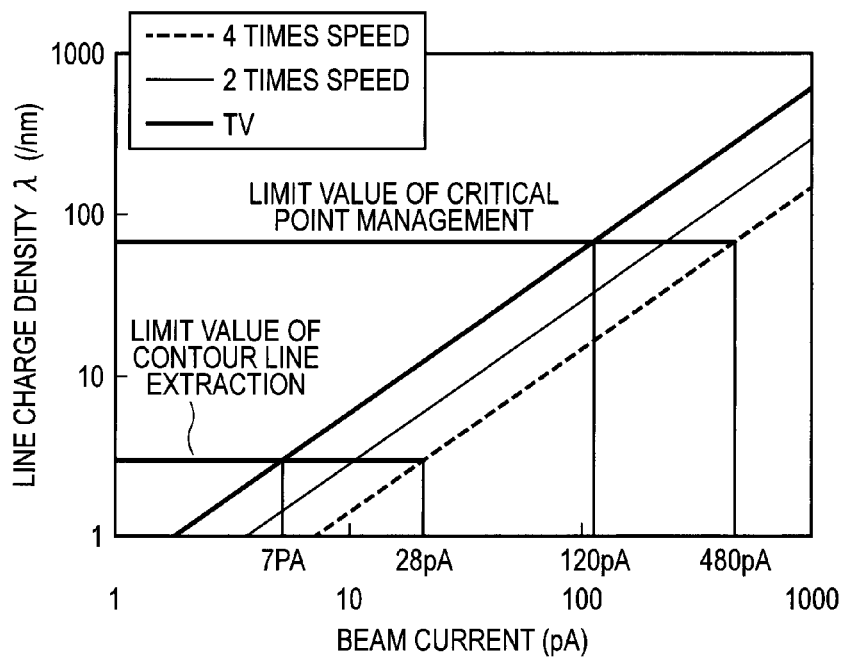
FIG. 9 is a diagram showing a scanning speed dependency of a line charge density calculated from the number of electrons per unit length irradiated into a scanning line.

FIG. 9 shows a scanning speed dependency of a line charge density calculated from the number of electrons per unit length irradiated within a scanning line. A deflecting width is 1.2 μm, a scanning time period per one scanning line is 114 μs in TV, 57 μs in 2 times speed, and 28 μs in 4 times speed. When a contour line of a circuit pattern on a resist is extracted from a white band of an SEM image, there is a location at which the contour cannot be detected due to electrification.

A limit value of contour line extraction of comparing the contour line with a design pattern of a circuit, and a limit value of a line charge density of a critical point management which detects a defect from the contour line are shown. At four times speed at which a scanning time period per a scanning line becomes 28 μs in case of a beam current four times as much as a beam current of TV, the line charge density is not increased. When the beam current 4 times as much as the beam current of TV is used, a time period of acquiring an image is shortened to ¼ under a condition in which a total pixel number stays equal, and the number of detecting electrons per pixel stays equal. S/N of an image is not deteriorated with ¼ of time period of acquiring an image since the number of injecting electrons per pixel is equal.

Figure 10:
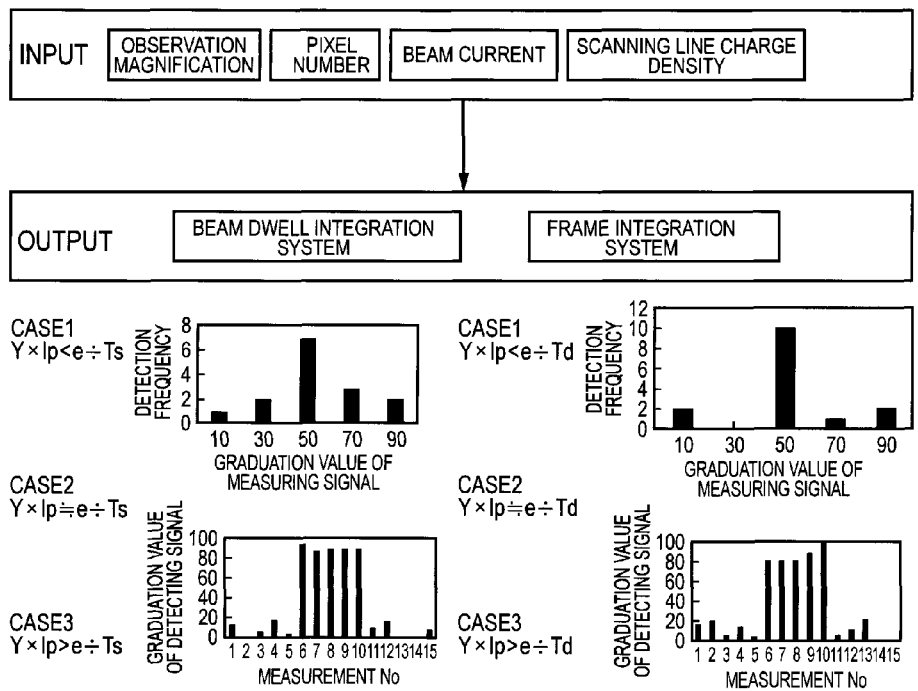
FIG. 10 is a flowchart of automatically selecting a beam dwell integration system or a frame integration system in setting the image quality improving processing shown in FIG. 7.

FIG. 10 shows a flow of automatically deriving 202 of set image quality improving processing by inputting 201 of set beam current, observation pixel number, and frame integration in the setting and executing procedure shown in FIG. 7. When an observation magnification, a pixel number, a beam current, and a scanning line charge density are inputted, beam dwell time Td is automatically derived. There are selected a beam dwell integration system and a frame integration system based on the number of secondary electrons which is calculated by dividing a product of a set beam current Ip by a yield Y which is a rate of emitting a secondary electron from a sample by an elementary electric charge. There is used an electron counting method in CASE1 in which the number of secondary electrons per a sampling time period, or beam dwell time is less than 1, an AC method or an electron counting method in CASE2 in which the number of secondary electrons is about 1, or an analog method in CASE3 in which the number of secondary electrons exceeds 1. There can automatically be selected a beam dwell integration system in which the set beam current depends on the number of electrons injected during sample time Ts, or there can automatically selected a frame integration system which depends on the number of electrons injected during Td by CASE classification described above.

Figure 11:
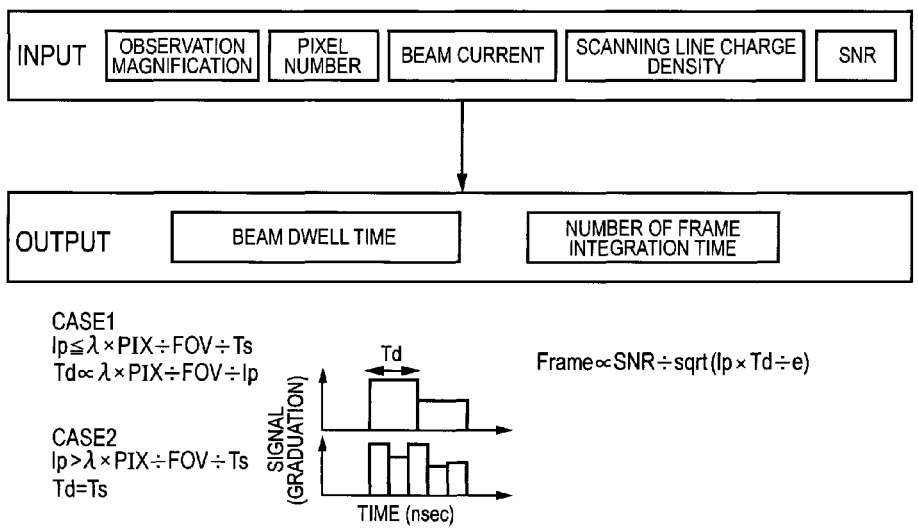
FIG. 11 is a flowchart of automatically deriving a beam dwell time period or the number of times of frame integration in setting the image quality improving processing shown in FIG. 7.

FIG. 11 shows a flow of automatically deriving 202 of set image quality improving processing by inputting 201 of set beam current, observation pixel number, and frame integration of the setting and executing procedure shown in FIG. 7. According to the present embodiment, beam dwell time Td and the number of times of frame integration can automatically be derived by inputting an observation magnification, a pixel number PIX, a beam current Ip, a scanning line charge density λ, and SNR of the observed image. That is, in a case where the set beam current Ip is smaller than a product of the pixel size calculated from a deflection width FOV and the pixel number PIX by which the number of electrons injected during sample time Ts is determined by an observation magnification by the scanning line charge density (CASE1), Td is made to be proportional to a value of dividing a product of the scanning line charge density by the pixel number by the detection width FOV and the beam current. On the other hand, when the set beam current Ip is larger than the number of electrons injected during the sampling time Ts multiplied by the scanning line charge density (CASE2), there is set a value of shortest beam dwell time which can be set by making Td=Ts.

When various samples such as a semiconductor device and a magnetic disk are inspected using the charged particle beam microscope shown in the present embodiment, images which emphasize contrasts of a hole bottom and a groove bottom can be obtained.

As described above, the present embodiment can provide a charged particle beam microscope which can acquire images emphasizing contrasts of a hole bottom and a groove bottom in a short period of time in inspecting various samples of a semiconductor device, a magnetic disk and the like by selecting a measurement processing method in accordance with the number of electrons detected per sampling time of one pixel. The embodiment can also provide a charged particle beam microscope which can acquire an image emphasizing a shadow contrast in a short period of time.

A detailed explanation has been given of the present invention as described above, and main modes of the invention will be enumerated as follows.

(1) A charged particle beam microscope including a charged particle source, a stage of mounting a sample, a charged particle optical system of irradiating the sample on the stage with a beam of a charged particle generated by the charged particle source, a detector of detecting a detected particle from the sample caused by the beam, and controlling means of controlling these, the charged particle beam microscope being featured in further including:

a beam dwell integration selector of determining a beam dwell integration method of detecting the detected particle caused by the beam, a beam dwell integrator of carrying out an integration in accordance with a determination of the beam dwell integration selector, a selector of a frame integration of determining a frame integration method, and a frame integrator of carrying out an integration in accordance with a determination of the selector of frame integration, wherein when the number of the detected particles which can be detected by the detector in sampling the detected particle caused by the beam is less than one piece, in a procedure of calculating the brightness graduation of one pixel within a beam dwell time period, a value adjusted by counting the number of times at which the brightness graduation falls within a set range is outputted.

(2) The charged particle beam microscope described in (1), featured in outputting the value adjusted by counting the number of times at which the brightness graduation falls within the set range in the procedure of calculating the brightness graduation in the frame integration using the frame integrator when the number of the detected particles which can be detected during the beam dwell time for measuring the brightness graduation of one pixel is less than one piece.

(3) The charged particle beam microscope described in (1), featured in outputting a peak value of a frequency distribution of the brightness graduation within the set range in the procedure of calculating the brightness graduation of one pixel within the beam dwell time period when the number of the detected particles which can be detected in one sampling is one piece.

(4) The charged particle beam microscope described in (1), featured in outputting a peak value of a frequency distribution of the brightness graduation within the set range in the procedure of calculating the brightness graduation in the frame integration using the frame integrator when the number of the detected particles which can be detected during the beam dwell time period of measuring the brightness graduation of one pixel is one piece.

(5) The charged particle beam microscope described in (1) described above, featured in outputting an average value of the brightness graduation in the procedure of calculating the brightness graduation in the frame integration using the frame integrator when the number of the detected particles which can be detected during the beam dwell time period of measuring the brightness graduation of one pixel exceeds one piece.

(6) The charged particle beam microscope described in (1) described above, featured in outputting an average value of the brightness graduation in the procedure of calculating the brightness graduation in the frame integration using the frame integrator when the number of electrons which can be detected during the beam dwell time of measuring the brightness graduation of one pixel exceeds one piece.

(7) The charged particle beam microscope described in (1) described above, featured in changing to output a peak value of a frequency distribution of the brightness graduation within the set range, or a value adjusted by counting the number of times at which the brightness graduation falls in the set range from an average value of the brightness graduation in the procedure of calculating the brightness graduation in the frame integration using the frame integrator in a case where a dispersion in the brightness graduation at each beam dwell time in the frame integration exceeds a threshold by pertinently adjusting a gain and an offset of the detector.

(8) A charged particle beam microscope including a charged particle source, a stage of mounting a sample, a charged particle optical system of irradiating the sample on the stage with a beam of a charged particle generated by the charged particle source, a detector of detecting a detected particle from the sample caused by the beam, displaying means, and controlling means of controlling these, the charged particle beam microscope being featured in that the displaying means displays a screen of setting an image quality improving processing.

(9) The charged particle beam microscope described in (8) described above, featured in that the displaying means displays an analog average value of a detecting signal at each pixel or a graduation value of the detecting signal, and a beam dwell integration counting number at each pixel.

(10) The charged particle beam microscope described in (9) described above, featured in that the number of the detected particles detected by the detector is larger in the pixel displayed by the analog average value of the detecting signal or the graduation value of the detecting signal than in the pixel displayed by the counting beam dwell integration counting number.

LIST OF REFERENCE SIGNS

1 . . . recessed and protruded portion of sample surface, 2 . . . electron beam, 3 . . . secondary particle (secondary electron), 4 . . . detector, 5 . . . inclination angle of recessed and protruded portion of sample surface, 6 . . . elevation angle component in direction of emitting secondary particle, 7 . . . shadow image provided by detector, 11 . . . electron beam, 12 . . . contour line of hole, 13 . . . schematic view of hole bottom observation image, 14 . . . contour line of groove, 15 . . . schematic view of groove bottom observation image, 101 . . . vacuum cabinet, 102 . . . electron optics system, 103 . . . electron optics system control device, 104 . . . host computer, 105 . . . operation table, 106 . . . displaying means, 110 . . . electron beam, 111 . . . electron source, 112 . . . deflector, 113 . . . objective lens, 114 . . . sample, 115 . . . secondary particle (secondary electron), 116 . . . booster magnetic path member, 117 . . . reflecting member, 118 . . . subsidiary particle (tertiary particle), 119 . . . central detector, 130 . . . drawing electrode, 131 . . . accelerating electrode, 132 . . . coil, 132' . . . control magnetic path member, 133 . . . yoke member, 134 . . . control magnetic path power source, 135 . . . booster magnetic path power source, 140 . . . stage, 141 . . . stage power source, 148 . . . central detector power source, 151 . . . brightness/contrast control circuit, 152 . . . A/D converter, 153 . . . beam dwell integration selector, 154 . . . beam dwell integrator, 155 . . . frame integration selector, 156 . . . frame integrator, 157 . . . image improving processing unit, 158 . . . observed image displaying unit, 159 . . . preserving unit of observed image, 171 . . . detecting signal amplification, 172 . . . brightness/contrast control, 173 . . . A/D conversion, 174 . . . selection of beam dwell integration, 175 . . . beam dwell integration, 176 . . . selection of frame integration, 177 . . . frame integration, 178 . . . image quality improving processing, 179 . . . display and preservation of observed image, 180 . . . schematic view of groove bottom observation image, 181 . . . contour line of groove, 182 . . . schematic view of groove bottom observation image, 183 . . . contour line of groove, 200 . . . advance preparation of sample observation, 201 . . . setting of beam current, observed pixel number, frame integration, 202 . . . setting of image quality improving processing, 203 . . . Brightness Contrast adjustment, 204 . . . observed image acquisition, 205 . . . determination of image quality improving processing, 206 . . . determination of observation condition, 207 . . . determination of end of observation, 208 . . . end of observation

The invention claimed is:
1. A charged particle beam microscope comprising:
a charged particle source;
a stage that mounts a sample;

a charged particle optical system that irradiates the sample on the stage with a charged particle beam generated by the charged particle source;

a detector that detects a particle emitted from the sample irradiated by the beam;

a controller that controls the charged particle source, the stage, the charged particle optical system, and the detector; and a processor that:
- determines a beam dwell integration method for detecting the particle emitted from the sample;
- carries out a beam dwell integration in accordance with the determined beam dwell integration method;
- determines a frame integration method; and
- carries out a frame integration in accordance with the frame integration method;

wherein when only one particle can be detected by the detector during a beam dwell time period, the processor changes the beam dwell integration method and the frame integration method.

2. The charged particle beam microscope according to claim 1, wherein when only one particle can be detected by the detector during the beam dwell time period, the processor determines a peak value of a frequency distribution of a brightness graduation within a set range.

3. The charged particle beam microscope according to claim 1, wherein when more than one particle can be detected by the detector during the beam dwell time period, the processor determines an average value of a brightness graduation.

4. The charged particle beam microscope according to claim 1, wherein when more than one electron can be detected by the detector during the beam dwell time period, the processor determines an average value of a brightness graduation.

5. The charged particle beam microscope according to claim 1, wherein when a dispersion in a brightness graduation for each beam dwell time period exceeds a threshold, the processor outputs a peak value of a frequency distribution of the brightness graduation within a set range, or a value adjusted by counting a number of times at which the brightness graduation falls within the set range from an average value of the brightness graduation, by adjusting a gain and an offset of the detector.

* * * * *